United States Patent [19]

Salek et al.

[11] Patent Number: 5,185,478
[45] Date of Patent: * Feb. 9, 1993

[54] MANUFACTURE OF NEOPENTYL GLYCOL (IIA)

[75] Inventors: Jeffrey S. Salek, Oakdale Boro; Joseph Pugach, Monroeville Boro, both of Pa.

[73] Assignee: Aristech Chemical Corporation, Pittsburgh, Pa.

[*] Notice: The portion of the term of this patent subsequent to Sep. 1, 2009 has been disclaimed.

[21] Appl. No.: 868,897

[22] Filed: Apr. 16, 1992

Related U.S. Application Data

[63] Continuation-in-part of Ser. No. 716,177, Jul. 17, 1991, abandoned.

[51] Int. Cl.$^5$ .................. C07C 31/18; C07C 45/00; C07C 69/66
[52] U.S. Cl. .................. 568/853; 568/881; 568/463; 568/464; 560/179
[58] Field of Search .............. 568/853, 881, 457, 458, 568/463, 464; 560/179

[56] References Cited

U.S. PATENT DOCUMENTS

| | | | |
|---|---|---|---|
| 2,135,063 | 11/1938 | Walker et al. | 260/635 |
| 2,317,456 | 4/1943 | Hanford et al. | 260/602 |
| 2,778,858 | 1/1957 | Meinhofer | 260/635 |
| 2,786,083 | 3/1957 | Wyler | 260/635 |
| 2,811,562 | 10/1957 | Hagemeyer, Jr. | 260/602 |
| 3,340,312 | 9/1967 | Duke, Jr. et al. | 260/635 |
| 3,504,042 | 3/1970 | Shimono et al. | 260/635 |
| 3,808,280 | 4/1974 | Merger et al. | 260/635 A |
| 3,876,706 | 4/1975 | Levanevsky et al. | 260/602 |
| 3,920,760 | 11/1975 | Heinz | 260/635 A |
| 3,935,274 | 1/1976 | Jacobsen et al. | 260/602 |
| 3,975,450 | 8/1976 | Palmer et al. | 260/635 P |
| 4,219,508 | 8/1980 | Wagner | 568/463 |
| 4,851,592 | 7/1989 | Morris | 568/853 |
| 4,855,515 | 8/1989 | Morris et al. | 568/862 |
| 4,945,184 | 7/1990 | Pugach et al. | 568/313 |

FOREIGN PATENT DOCUMENTS 1017618  1/1966  United Kingdom .

Primary Examiner—Marianne M. Cintins
Assistant Examiner—Rebecca Cook
Attorney, Agent, or Firm—William L. Krayer

[57] ABSTRACT

Neopentyl glycol is made by reacting isobutyraldehyde with paraformaldehyde in the presence of a tertiary amine and cadmium or yttrium oxide; then hydrogenating the resulting reaction mixture containing hydroxypivaldehyde and at least about 20% 3-hydroxy-2,2-dimethylpropylhydroxypivalate.

12 Claims, No Drawings

MANUFACTURE OF NEOPENTYL GLYCOL (IIA)

RELATED APPLICATION

This application is a continuation-in-part of Ser. No. 716,177, filed Jun. 17, 1991, now abandoned entitled "Manufacture of Neopentyl Glycol (II)".

TECHNICAL FIELD

This invention relates to the manufacture of neopentyl glycol. In particular it relates to the manufacture of neopentyl glycol by reacting isobutyraldehyde with paraformaldehyde in the presence of a catalyst comprising one or more oxides selected from the group consisting of cadmium oxide and yttrium oxide and triethylamine or other lower alkyl tertiary amines, and hydrogenating the resulting mixture of hydroxypivaldehyde and hydroxyneopentylhydroxypivalate.

BACKGROUND ART

Prior to this invention, it has been known to make neopentyl glycol (2,2 dimethyl-1,3-dihydroxypropane, also known herein as NPG) by reacting formaldehyde with isobutyraldehyde (IBAL) and hydrogenating the resulting hydroxypivaldehyde (HPA). See U.S Pat. No. 4,855,515, for example, which recites the historical development of the reaction and emphasizes the use of a particular catalyst in the hydrogenation step. U.S. Pat. No. 3,808,280 discloses the use of triethylamine as a catalyst for the (aqueous) formaldehyde/IBAL reaction.

Each of the above references employs formaldehyde in the form of aqueous formaldehyde.

Paraformaldehyde is used by Snam S.p.A. in UK Pat. No. 1,017,618 to react with IBAL in the presence of a tertiary amine to produce a reaction product containing apparently predominantly HPA which may be hydrogenated to neopentyl glycol. No reference to our knowledge teaches the use of cadmium or yttrium oxide and paraformaldehyde with the accompanying advantages as explained below, and particularly to make hydroxyneopentylhydroxypivalate.

SUMMARY OF THE INVENTION

The present invention is a method of making 3-hydroxy-2,2-dimethylpropylhydroxypivalate, sometimes known as hydroxyneopentylhydroxypivalate (HNHP), and subsequently NPG, by reacting IBAL with paraformaldehyde in the presence of a tertiary amine catalyst, preferably triethylamine, and an oxide selected from the group consisting of cadmium and yttrium oxide to obtain a mixture of HNHP and HPA, and hydrogenating the HNHP/HPA mixture to obtain NPG. The HNHP/HPA mixture may be isolated, typically in the form of a white solid. Whether or not it is isolated and/or purified, it is conveniently hydrogenated in the form of a methanol solution, in the presence of a copper chromite catalyst, for example, to obtain the desired neopentyl glycol.

A specific reaction may be described as follows: The reaction is performed in a reflux apparatus wherein one equivalent of IBAL, one equivalent of paraformaldehyde, 0.01 equivalent of cadmium oxide, and about 0.04 to 0.05 equivalent of triethylamine have been placed. The reaction mixture is stirred at the reflux temperature of IBAL (about 63°–64° C.) for about one to six hours. The clear yellow molten liquid (a mixture of HNHP and HPA) is decanted from the cadmium oxide co-catalyst. The HNHP/HPA mixture is hydrogenated in any conventional (convenient) manner such as by passing a methanol solution over a copper chromite catalyst at about 100°–200° C. and about 500–3000 psig., to obtain the NPG, which is finally purified by recrystallization or distillation.

More generally, with one equivalent of IBAL we may place in a reaction vessel from about 0.5 to about 2 equivalents of paraformaldehyde, about 0.001 to about 0.1 (preferably about 0.005 to about 0.05) equivalent of cadmium oxide or yttrium oxide and about 0.01 to about 0.1 (preferably 0.02 to about 0.08) equivalent of a tertiary amine. The reaction mixture is stirred until the desired conversion of IBAL is obtained. The resulting HNHP/HPA mixture may be hydrogenated with or without further purification. A reaction product containing at least about 20% HNHP is readily hydrogenated.

As is known in the art, if the amine chosen has a boiling point lower than the boiling point (reflux temperature) of IBAL, pressure may be used.

Our invention provides a process in which water is minimized and is therefore relatively easier to perform since it does not require the separation and/or disposal of water; the process is also considerably more efficient than prior art processes, since the HNHP/HPA product can be used directly, i.e. without an arduous separation or purification process, for the hydrogenation step to NPG. Mild hydrogenation conditions, that is, temperatures as low as 100° C. and pressures as low as 500 psig, may be used. The process is also more efficient in that fewer by-products are made and indeed one need not be concerned with the complications of by-products. Under properly controlled conditions, paraformaldehyde is easier and safer to store than aqueous formaldehyde. Substantially reduced emissions may be expected.

The metal oxide co-catalyst can be removed from the HNHP reaction product before it is hydrogenated, by filtration or any convenient means for recycling. The reaction may also be performed over a bed of catalyst.

We may use various tertiary amines. Specifically, we may use as catalysts any tertiary amines of the general formula $R^1R^2R^3N$ where $R^1$, $R^2$, and $R^3$ are alkyl groups of the general formula $C_1$–$C_{15}$ and $R^1$ and $R^2$ may form a substituted or unsubstituted cyclic group having from 5 to about 15 carbon atoms.

DETAILED DESCRIPTION OF THE INVENTION

Table I recites the results of similar experiments utilizing:

| Reagent | Equivalents |
| --- | --- |
| IBAL | 1.00 |
| Paraformaldehyde | 1.00 |
| Triethylamine | 0.050 |
| Metal oxide | 0.010 |

With the exception of #16, the reactions were terminated 1 hour after the IBAL quit refluxing and then analyzed by G.C. Everything else was done as similarly as possible so that the effect of the metal oxides could be compared.

It will be seen that the selectivity for HNHP was quite striking in the cases of cadmium oxide and yttrium oxide. It will be noted from Example 16 that a relatively long reaction time favors the production of HNHP.

TABLE I

| Examples | Co-Catalyst | % IBAL Conv. | % HPA Sel. | % "HNHP" Sel.* | Reaction Time (h) | Comments |
|---|---|---|---|---|---|---|
| 1. | None | 92 | 92 | 3.7 | 2.42 | Control |
| 2. | $Nb_2O_5$ | 97 | 96 | 1.3 | 2.08 | |
| 3. | $ZrO_2$ | 98 | 97 | 1.0 | 2.00 | |
| 4. | $MnO_2$ | 97 | 90 | 7.3 | 1.92 | |
| 5. | $As_2O_3$ | 97 | 97 | 1.3 | 2.00 | |
| 6. | CuO | 97 | 96 | 2.4 | 1.92 | |
| 7. | $TiO_2$ | 99 | 98 | 0.3 | 1.17 | |
| 8. | CdO | 97 | 66 | 29.0 | 1.08 | |
| 9. | $CeO_2$ | 97 | 94 | 0.6 | 1.33 | |
| 10. | NiO | 96 | 91 | 7.0 | 1.58 | |
| 11. | $Sm_2O_3$ | 99 | 91 | 1.1 | 2.00 | |
| 12. | Silica Gel | 97 | 97 | 1.7 | 2.50 | |
| 13. | $Cr_2O_3$ | 99 | 95 | 2.7 | 1.58 | |
| 14. | $Bi_2O_3$ | 99 | 96 | 2.1 | 2.50 | |
| 15. | $Y_2O_3$ | 95 | 58 | 31.5 | 1.75 | |
| 16. | $Y_2O_3$ | 99 | 10 | 67.6 | 6.0 | |

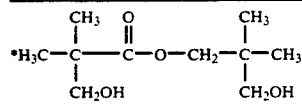

EXAMPLE 17

80.0 g of IBAL, 38.8 g of paraformaldehyde, 5.6 g of triethylamine, and 2.5 g of $Y_2O_3$ were charged with stirring into a 250 mL 3-neck roundbottom flask equipped with a reflux condenser and stirbar. The apparatus was lowered into a heated oil bath (80° C.) giving moderate IBAL reflux within minutes. After 6 h, the reaction mixture was filtered and diluted in 400 g of methanol. The reaction effluent was charged to an autoclave together with 16.0 g of $CuCr_2O_4$ and hydrogenated for 1.5 h at 150° C. followed by 1.5 h at 180° C. using 1000 psig $H_2$. The results are summarized in Table II.

TABLE II

| *GC Analysis of Hydrogenated Effluent | | % HNHP Conversion |
|---|---|---|
| % isobutyl alcohol | 2.33 | 56.2% |
| % triethylamine | 5.42 | |
| % methyl hydroxypivalate | 16.12 | |
| % hydroxypivaldehyde | 0.00 | |
| % neopentyl glycol | 44.32 | |
| % NPG monoisobutyrate | 3.68 | |
| % hydroxyneopentyl hydroxypivalate | 25.77 | |
| % others | 2.36 | |

*GC area %'s are reported on a methanol-free basis.

EXAMPLE 18

80.0 g of IBAL, 38.8 g of paraformaldehyde, 5.6 g of triethylamine, and 2.5 g of $Y_2O_3$ were charged with stirring into a 250 mL 3-neck roundbottom flask equipped with a reflux condenser and stirbar. The apparatus was lowered into a heated oil bath (80° C.) giving moderate IBAL reflux within minutes. After 6 h, the reaction mixture was filtered and diluted in 400 g of methanol. The reaction effluent was charged to an autoclave together with 16.0 g of $CuCr_2O_4$ and hydrogenated for 2 h at 1000 psig $H_2$ (sample A) followed by 2 h at 2000 psig $H_2$ using a temperature of 180° C. (sample B). The results are summarized in Table III.

TABLE III

| *GC Analysis of Hydrogenated Effluent | sample A | sample B | % HNHP Conversion sample A | sample B |
|---|---|---|---|---|
| % isobutyl alcohol | 1.74 | 2.56 | 51.6% | 84.3% |
| % triethylamine | 4.56 | 4.48 | | |
| % methyl hydroxypivalate | 14.27 | 23.89 | | |
| % hydroxypivaldehyde | 0.00 | 0.00 | | |
| % neopentyl glycol | 41.19 | 53.52 | | |
| % NPG monoisobutyrate | 2.63 | 1.38 | | |
| % hydroxyneopentyl hydroxypivalate | 33.31 | 10.77 | | |
| % others | 2.30 | 3.40 | | |

*GC area %'s are reported on a methanol-free basis.

EXAMPLE 19

HNHP hydrogenolysis compared to methylisobutyrate hydrogenolysis:

The following solutions were prepared:

| (A) | NPG | 47.6 wt. % |
|---|---|---|
| | HNHP | 2.4 wt. % |
| | triethylamine | 2.3 wt. % |
| | methanol | 47.6 wt. % |
| (B) | methylisobutyrate | 5 wt. % |
| | methanol | 95 wt. % |

A batch hydrogenation was performed on each solution using 1.4 wt. % $CuCr_2O_4$ at 150° C. for 1 h at 1000 psig $H_2$. Ester hydrogenolysis was monitored. The results follow in Table IV. These results are surprising in that the ester impurities indigenous to the process in this invention are more easily hydrogenolyzed than a typical ester such as methylisobutyrate; they are also surprising in that we are able to hydrogenate easily at relatively low temperatures and pressures. This allows the recovery of high purity NPG product by simple distillation.

TABLE IV

| Ester | % Conversion |
|---|---|
| HNHP | 65.7% |

TABLE IV-continued

| Ester | % Conversion |
|---|---|
| Methylisobutyrate | 1.4% |

We claim:

1. Method of making hydroxypivaldehyde and 3-hydroxy-2,2-dimethyl propyl hydroxypivalate comprising reacting paraformaldehyde with isobutyraldehyde in the presence of a catalyst comprising a tertiary amine and an oxide selected from the group consisting of cadmium oxide and yttrium oxide.

2. Method of making neopentyl glycol comprising reacting paraformaldehyde with isobutyraldehyde in the presence of a catalyst comprising a tertiary amine and an oxide selected from the group consisting of cadmium oxide and yttrium oxide to obtain a reaction product containing hydroxypivaldehyde and at least about 20% 3-hydroxy-2,2-dimethylpropylhydroxypivalate and hydrogenating the reaction product.

3. Method of claim 1 wherein the tertiary amine is triethylamine.

4. Method of claim 2 wherein the tertiary amine is triethylamine.

5. Method of claim 1 wherein the ratio of paraformaldehyde to isobutyraldehyde is about 0.5:1 to about 2:1.

6. Method of claim 2 including the step of recovering the oxide catalyst prior to hydrogenation of the 3-hydroxy-2,2-dimethylpropylhydroxypivalate/hydroxypivaldehyde mixture.

7. Method of claim 1 wherein the amine has the formula $R^1R^2R^3N$ where $R^1$, $R^2$, and $R^3$ are alkyl groups of the general formula $C_1-C_{15}$ and $R^1$ and $R^2$ may form a subsituted or unsubstituted cyclic group having from 5 to about 15 carbon atoms.

8. Method of claim 2 wherein the amine has the formula $R^1R^2R^3N$ where $R^1$, $R^2$, and $R^3$ are alkyl groups of the general formula $C_1-C_{15}$ and $R^1$ and $R^2$ may form a subsituted or unsubstituted cyclic group having from 5 to about 15 carbon atoms.

9. Method of claim 2 wherein the hydrogenation step is performed by (a) mixing the reaction product containing hydroxypivaldehyde and at least 20% HNHP with at least about 20% of an alcohol of the formula RR'CHOH where R and R' are independently selected from the group consisting of hydrogen and alkyl groups having one to five carbon atoms and (b) contacting the mixture with hydrogen in the presence of a hydrogenation catalyst.

10. Method of claim 9 wherein the alcohol is methanol.

11. Method of claim 9 wherein the hydrogenation is conducted at a pressure of about 500 to 3000 psig and a temperature of about 100° to 200° C.

12. Method of claim 9 wherein the hydrogenation catalyst comprises copper chromite.

* * * * *